United States Patent
Striemer et al.

(10) Patent No.: US 10,391,219 B2
(45) Date of Patent: *Aug. 27, 2019

(54) NANOPOROUS SILICON NITRIDE MEMBRANES, AND METHODS FOR MAKING AND USING SUCH MEMBRANES

(71) Applicant: SiMPore, Inc., West Henrietta, NY (US)

(72) Inventors: Christopher C. Striemer, Rochester, NY (US); Jon-Paul DesOrmeaux, Rochester, NY (US)

(73) Assignee: SiMPore, Inc., West Henrietta, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,757

(22) Filed: Oct. 13, 2017

(65) Prior Publication Data
US 2018/0147336 A1    May 31, 2018

Related U.S. Application Data

(63) Continuation of application No. 14/911,879, filed as application No. PCT/US2014/051316 on Aug. 15, 2014, now Pat. No. 9,789,239.
(Continued)

(51) Int. Cl.
*B01D 67/00* (2006.01)
*B01D 71/02* (2006.01)
(Continued)

(52) U.S. Cl.
CPC ......... *A61M 1/1631* (2014.02); *B01D 63/088* (2013.01); *B01D 67/0037* (2013.01);
(Continued)

(58) Field of Classification Search
None
See application file for complete search history.

(56) References Cited

U.S. PATENT DOCUMENTS

| 5,753,014 A | 5/1998 | Van Rijn |
| 6,547,973 B2 | 4/2003 | Field |

(Continued)

FOREIGN PATENT DOCUMENTS

| JP | H05179416 A | 7/1993 |
| JP | 2004209632 A | 7/2004 |
| JP | 2009064935 A | 3/2009 |

OTHER PUBLICATIONS

Striemer, C.C., et al., Charge- and size-based separation of macromolecules using ultrathin silicon membranes, Nature, Feb. 15, 2007, vol. 445, pp. 749-753.
(Continued)

*Primary Examiner* — Shamim Ahmed
(74) *Attorney, Agent, or Firm* — Hodgson Russ LLP

(57) ABSTRACT

Provided are nanoporous silicon nitride membranes and methods of making such membranes. The membranes can be part of a monolithic structure or free-standing. The membranes can be made by transfer of the nanoporous structure of a nanoporous silicon or silicon oxide film by, for example, reactive ion etching. The membranes can be used in, for example, filtration applications, hemodialysis applications, hemodialysis devices, laboratory separation devices, multiwell cell culture devices, electronic biosensors, optical biosensors, active pre-concentration filters for microfluidic devices.

17 Claims, 11 Drawing Sheets

Related U.S. Application Data

(60) Provisional application No. 61/866,660, filed on Aug. 16, 2013.

(51) Int. Cl.

| | | |
|---|---|---|
| *B44C 1/22* | (2006.01) | |
| *A61M 1/16* | (2006.01) | |
| *B01D 63/08* | (2006.01) | |
| *B01D 69/06* | (2006.01) | |
| *B82Y 40/00* | (2011.01) | |
| *B01D 61/24* | (2006.01) | |

(52) U.S. Cl.
CPC ......... *B01D 67/0062* (2013.01); *B01D 69/06* (2013.01); *B01D 71/02* (2013.01); *B01D 61/243* (2013.01); *B82Y 40/00* (2013.01)

(56) References Cited

U.S. PATENT DOCUMENTS

| | | | |
|---|---|---|---|
| 8,182,590 | B2 | 5/2012 | Striemer et al. |
| 2004/0124092 | A1 | 7/2004 | Black et al. |
| 2007/0224235 | A1 | 9/2007 | Tenney et al. |
| 2008/0223795 | A1 | 9/2008 | Bakajin et al. |
| 2008/0311375 | A1 | 12/2008 | Harnack et al. |
| 2010/0084333 | A1 | 4/2010 | Hoogerwerf |
| 2011/0042301 | A1 | 2/2011 | Zhang et al. |
| 2012/0037591 | A1 | 2/2012 | Tringe et al. |
| 2013/0180867 | A1 | 7/2013 | Rosenstein et al. |
| 2013/0092541 | A1 | 8/2013 | Drndic et al. |
| 2014/0021133 | A1 | 1/2014 | Siwy et al. |

OTHER PUBLICATIONS

Nabar, B.P., et al., A nanoporous silicon nitride membrane using a two-step lift-off pattern transfer with thermal nanoimprint lithography, Journal of Micromechanics and Microengineering, 2012, vol. 22, 8 pages.

NANOPOROUS SILICON NITRIDE MEMBRANES, AND METHODS FOR MAKING AND USING SUCH MEMBRANES

CROSS-REFERENCE TO RELATED APPLICATIONS

This application is a continuation application of U.S. application Ser. No. 14/911,879, filed on Feb. 12, 2016, now U.S. Pat. No. 6,789,239, which is a national stage entry of PCT/US14/51316, filed on Aug. 15, 2014, which claims priority to U.S. provisional patent application No. 61/866,660, filed Aug. 16, 2013, the disclosures of which are incorporated herein by reference in their entirety.

FIELD OF THE DISCLOSURE

This invention relates to formation of porous membranes and, more particularly, to forming porous silicon nitride (SiN) membranes.

BACKGROUND OF THE DISCLOSURE

It is difficult to form membranes with very small or thin dimensions using current techniques. First, the mechanical strength of porous nano-crystalline Si (pnc-Si) membranes may be limited to freely suspended areas under approximately 1 mm$^2$ if the pnc-Si membrane is exposed to differential pressures exceeding 5 psi. 5 psi may represent a differential pressure that a pnc-Si membrane is likely to survive during an exemplary device assembly. Membrane deformation, such as that which occurs during exposure to certain differential pressures, is one factor that affects mechanical failure. Second, while chips with active areas as large as 1 cm$^2$ can be manufactured using multiple windows and scaffolding, the cost of such chips is too expensive for many commercial applications. This is at least partly due to the number of chips that can be placed on a wafer. In an instance, nearly half the cost of wafer production could be attributed to the time and cost of the etch step through the Si to expose the membrane from the backside. Chemical etch through a Si wafer to reach the membrane backside is the costliest step in current membrane production.

Increasing ultrathin nanocrystalline silicon membrane area, such as those thinner than approximately 100 nm, through improvements in mechanical properties may be limited to freestanding areas of less than 10 mm$^2$. Thus, large area membrane devices may require multiple membrane windows, which increases the cost per device as the fraction of the wafer that is occupied by each device increases. Methods that reduce the cost of membrane production may be needed if larger membranes are to become commercially viable. What is needed is an improved porous membrane and an improved method of making or using such a porous membrane.

SUMMARY OF THE DISCLOSURE

Provided are methods for forming nanoporous SiN layers. The nanoporous SiN membranes can be part of a monolithic structure or a free-standing membrane. Thus, the nanoporous SiN membrane may be supported by a Si wafer or may be independent of the Si wafer.

In an embodiment, a method for forming a nanoporous SiN layer comprises: forming a pnc-Si layer or porous silicon oxide layer that is disposed on an SiN layer, and etching the SiN layer such that a nanoporous SiN layer is formed. The etching may be carried out using reactive ion etching (RIE). The RIE may be carried out using at least one of CF$_4$, CHF$_3$, or Ar. The RIE may use O$_2$ or H$_2$ in addition to the aforementioned gases. In an embodiment, substantially all or all of the pnc-Si layer or the porous silicon oxide layer is removed during the etching. In embodiment, the method further comprises: forming an a-Si layer on the SiN layer, and forming the pnc-Si layer by performing a thermal treatment on the a-Si layer. In an embodiment the porous silicon oxide layer is formed from the pnc-Si layer.

In an embodiment, a method for forming a free-standing nanoporous SiN layer comprises: forming pores in an SiN layer, where the SiN layer is disposed on a first layer and the first layer is disposed on a second layer, where the first layer is selected from the group consisting of Si and an oxide; and removing the first layer from between the SiN layer and the second layer such that a free-standing nanoporous SiN layer is formed. In an embodiment, the first layer comprises SiO$_2$ and the second layer comprises Si. In an embodiment, the second layer comprises a material selected from the group consisting of stainless steel, Al$_2$O$_3$, SiO$_2$, and glass. In an embodiment, the first layer is Si and the removing comprises using XeF$_2$. In an embodiment, the forming comprises: forming a pnc-Si layer or a porous silicon oxide layer on the SiN layer, and etching the pnc-Si layer or the porous silicon oxide layer such that the pores in the SiN layer are formed. In an embodiment, the porous silicon oxide layer is formed from the pnc-Si layer. In an embodiment, the etching comprises reactive ion etching. The etching may be carried out using reactive ion etching (RIE). The RIE may be carried out using at least one of CF$_4$, CHF$_3$, or Ar. The RIE may use O$_2$ or H$_2$ in addition to the aforementioned gases. In an embodiment, the method further comprises: forming an a-Si layer on the SiN layer, and forming the pnc-Si layer by performing a thermal treatment on the a-Si layer. In an embodiment, substantially all or all of the pnc-Si layer is removed during the etching. For example, buffered oxide etchant is used to remove a thin silicon layer. As another example, aqueous potassium hydroxide etchant or EDP etchant is applied to remove the pnc-Si layer.

In an embodiment, a method for forming a free-standing nanoporous SiN layer comprises: forming pores in an SiN layer, where the SiN layer is disposed on an Si layer and the Si layer is disposed on a second layer, and removing the Si layer between the SiN layer and the second layer using XeF$_2$ such that a free-standing nanoporous SiN layer is formed. In an embodiment, the second layer comprises a material selected from the group consisting of stainless steel, Al$_2$O$_3$, SiO$_2$, and glass. In an embodiment, the forming comprises: forming a pnc-Si layer or a porous silicon oxide layer on the SiN layer, and etching the pnc-Si layer or the porous silicon oxide layer such that the pores in the SiN layer are formed. In an embodiment, the porous silicon oxide layer is formed from the pnc-Si layer. The etching may be carried out using reactive ion etching (RIE). The RIE may be carried out using at least one of CF$_4$, CHF$_3$, or Ar. The RIE may use O$_2$ or H$_2$ in addition to the aforementioned gases. In an embodiment, the method further comprises: forming an a-Si layer on the SiN layer, and forming the pnc-Si layer by performing a thermal treatment on the a-Si layer. In an embodiment, substantially all or all of the pnc-Si layer is removed during the etching. For example, buffered oxide etchant is used to remove a thin silicon layer. As another example, aqueous potassium hydroxide etchant or EDP etchant is applied to remove the pnc-Si layer.

The nanoporous SiN membranes can be used in a variety of applications. These membranes may be used in, for example, hemodialysis devices, laboratory separation devices, multi-well cell culture devices, electronic biosensors, optical biosensors, active pre-concentration filters for microfluidic devices, or other applications.

By "substantially all or all of the pnc-Si layer is removed during the etching" as used herein it is meant that no pnc-Si is observed optically or by ellipsometry after the etch process.

DESCRIPTION OF THE DRAWINGS

For a fuller understanding of the nature and objects of the invention, reference should be made to the following detailed description taken in conjunction with the accompanying drawings.

DETAILED DESCRIPTION OF THE DISCLOSURE

Figure 2:
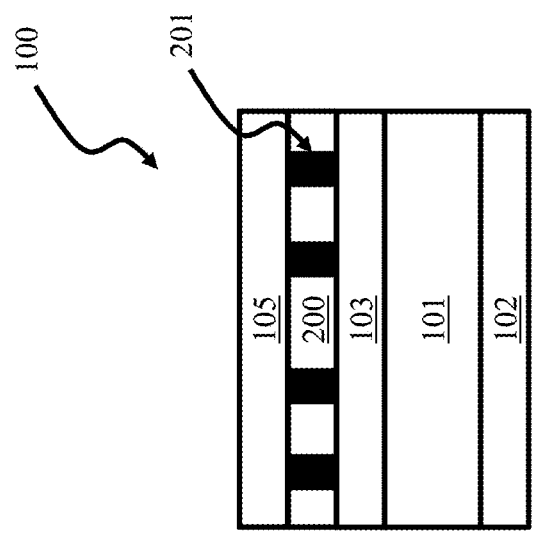
FIGS. 1-5 are schematic representations of a first example of an SiN membrane manufacturing process.

The present disclosure provides nanoporous SiN membranes and methods of making such membranes. Also provided are uses of such membranes.

SiN membranes have numerous advantages over, for example, pnc-Si membranes. First, SiN is stronger (e.g., has a higher burst pressure or increased resistance to deflection) than pnc-Si at an equivalent thickness, which may result in the membrane tolerating increased differential pressures. For example, an SiN membrane can withstand a differential pressure three times larger than pnc-Si. The Young's modulus of SiN is three times that of pnc-Si and the maximum deflection of a membrane is inversely proportional to the Young's modulus. The maximum deflection for membranes also increases as the third power of the membrane thickness increases, which further can help a membrane withstand a burst of pressure. Accordingly, a 30 nm thick nanoporous SiN membrane may be approximately 20 times stronger than a 15 nm thick pnc-Si membrane. For example, a 30 nm thick nanoporous SiN membrane can resist 1 atm of differential pressure at areas of less than 5 mm$^2$. Larger device areas can be achieved by patterning more windows or by using thicker materials. Besides having increased strength, SiN also is more stable as a freestanding membrane than pnc-Si, which may enable formation of larger membranes.

Second, SiN is more resistive to KOH and ethylene diamine and pyrocatechol (EDP) Si etchants than pnc-Si, which may eliminate pinhole defects. SiN is also compatible with most wet chemistries, such as Piranha Clean (which is a mixture of sulfuric acid, peroxide, and water in an embodiment), post-etch standard clean 1 ("SC1," which is a mixture of ammonium hydroxide, peroxide, and water), buffered oxide etchant (BOE), or others known to those skilled in the art.

Third, SiN may be deposited using low pressure chemical vapor deposition (LPCVD) or other methods. These may be batch processes, which increase manufacturing throughput.

Use of these SiN membranes may lower manufacturing costs, improve the quality or size of the membranes, or enable new applications for these membranes. SiN membranes also are compatible with a broad range of solutions, including high-pH solutions. However, fabricating an SiN membrane with the desired porosity or size has been previously unknown. Fabricating membranes of other materials at larger sizes has proven difficult due to mechanical strength of these other materials and the high manufacturing costs.

In an aspect, the present disclosure provides a nanoporous SiN membrane. The nanoporous SiN membranes can be part of a monolithic structure or a free-standing membrane. Thus, the nanoporous SiN membrane may be supported by a Si wafer or may be independent of the Si wafer.

The SiN membrane can have a range of pore sizes and porosity. For example, the pores can be from 10 nm to 100 nm, including all values to the nm and ranges therebetween. The pores also can be 10 nm or less or even 1 nm or less. For example, the porosity can be from <1% to 40%, including all integer % values and ranges therebetween. In a particular embodiment, the SiN pore sizes range from approximately 5 nm to 80 nm and the SiN porosity ranges from 1% to 40%. Of course, other pore size and porosity values are possible and these are merely listed as examples.

The shape of the pores can be modified. For example, conical pores can be produced by reducing RIE etching time.

The SiN membrane can have a range of thickness. For example, the thickness of the membrane can be from 20 nm to 100 nm, including all values to the nm and ranges therebetween. Of course, other thickness values are possible and these are merely listed as examples.

In an embodiment, the SiN membrane is at least one layer of a layered structure on a substrate (i.e., part of a monolithic structure). For example, the membrane can be a layer on a silicon wafer. The membrane is at least partially free from contact with the adjacent layer (or substrate).

In another embodiment, the SiN membrane is a free-standing membrane. This membrane can have a range of sizes. For example, the membrane can have an area of up to 100 mm$^2$ and/or a length of up to 10 mm and a width of up to 10 mm when using a Si wafer for support. However, if the membrane is separated from the Si wafer, then a larger area may be available. For example, free-standing circular membranes with diameters of 4 inches, 6 inches, or 8 inches, which may correspond to the silicon wafer size, can be fabricated.

A membrane occupying an entire Si wafer, which is greater than 100 cm$^2$, can be produced by embodiments of the "lift-off" process discussed herein. For example, SU-8 photoresist and photo-crosslinkable polyethyle glycol may provide improved membrane support (also referred to herein as a "scaffold"). Use of such polymers is also advantageous because these polymers are biocompatible and can be used in, for example, cell culture arrays. The various dimensions of the support, such as opening sizes, bar thickness, or scaffold thickness, can be optimized. For example, the scaffolds or SiN membrane may be patterned to match the well density and spacing of multi-well plates or other cell culture arrays. The scaffold materials may vary and may not be limited solely to photoresist. For example, the scaffold may be fabricated of PVDF, PTFE, cellulose, nylon, PES, or any plastic, metal, or other material that can be laser cut or otherwise formed into a supporting mesh scaffold to support the SiN membrane. Other examples of suitable scaffold materials include fluorinated polymers (e.g., highly fluorinated polymers) or fluorinated photoresists (e.g., highly fluorinated photoresists).

In an aspect, the present disclosure provides a method of making a nanoporous SiN membrane. The methods are based on transfer of the nanoporous structure of a nanoporous silicon film (e.g., pnc-Si) or nanoporous silicon oxide film to a SiN film. Embodiments disclosed herein use a pore transfer process that uses pnc-Si or nanoporous silicon oxide film as a template for patterning SiN to have pores (also referred to as nanopores). Embodiments disclosed herein also use a process that lifts porous (also referred to as nanoporous) SiN membranes from the front surface of a Si wafer to avoid a through-wafer chemical etching process, which may be expensive and time consuming. This may result in production of membranes with increased area and membranes that are more mechanically robust. For example, the membrane may have an area as large as a 150 mm Si wafer, which is approximately 177 $cm^2$, an 200 mm Si wafer, or any glass or ceramic substrate that meets form factor and thermal requirements for a particular deposition, annealing, or liftoff process. The various steps disclosed herein may be performed on either a single wafer or batch of wafers.

In an embodiment, the method comprises: forming a nanoporous silicon film (e.g., pnc-Si film) or nanoporous silicon oxide film that is disposed on an SiN layer; etching said nanoporous silicon film (e.g., pnc-Si film) or nanoporous silicon oxide film such that pores in the SiN layer are formed during the etching. In another embodiment, the method further comprises the step of releasing the layer such that a free standing nanoporous SiN layer is formed. In an embodiment, the present disclosure provides a structure comprising a pnc-Si film as described herein disposed on a SiN film (a non-sacrificial film) as described herein.

The pnc-Si layer can be formed by methods known in the art. For example, the pnc-Si layer (e.g., layer 200 in FIG. 2) is formed by deposition of an amorphous silicon layer (e.g., layer 104 in FIG. 1) and subsequently depositing a silicon oxide layer (e.g., layer 105 in FIGS. 1 and 2) on the amorphous silicon layer. The amorphous silicon layer and silicon oxide layer are heat treated under conditions such that a pnc-Si layer is formed. The silicon oxide layer may be a sacrificial layer that is removed after formation of the pnc-Si layer. In an embodiment, the pnc-Si layer is formed as described in U.S. Pat. No. 8,182,590, the disclosure of which with respect to formation of pnc-Si layers is incorporated herein by reference.

In an embodiment, the pnc-Si mask is oxidized to form an $SiO_2$ mask, e.g., during a thermal process carried out prior to the RIE transfer process. Some or all of the pnc-Si mask may be converted to the $SiO_2$ mask during the oxidation, so some or none of the pnc-Si mask layer may remain. Depending on the source gas or gases used for the etching, this results in a $SiO_2$ mask layer with greater etch selectivity. The oxidation also may reduce the pore size of thicker pnc-Si films because oxidation increases the volume by approximately 60% and constricts the pores.

The membranes may be produced on materials other than Si. For example, the membranes may be produced on stainless steel, $Al_2O_3$, $SiO_2$, glass, or other materials known to those skilled in the art. Such materials may have certain surface roughness or temperature stability characteristics. For example, the surface roughness may be greater than a root means square (RMS) roughness of approximately 1 nm. However, this surface roughness may be limited based on degradation of the membrane quality for certain applications. Furthermore, these alternate materials may need to maintain structural integrity during pore formation because the membrane may achieve temperatures up to approximately 1000° C. Certain materials, such as fused $SiO_2$, $Al_2O_3$, or other materials known to those skilled in the art, may be used to withstand the heating process. Fused $SiO_2$ or $Al_2O_3$ both may be transparent to most of the spectrum generated by the heat lamps during the annealing process to create nanopores. However, other materials, such as Mylar®, Teflon®, or Al may be used if higher temperatures are localized at the membrane.

The membranes may be produced on round or rectangular surfaces. Use of a rectangular surface may enable conveyor-style or roll-to-roll style production of the membranes. While particular membrane dimensions are disclosed, larger membranes on the order of greater than approximately 1 $m^2$ may be possible using the methods disclosed herein.

The structure of a nanoporous silicon film (e.g., pnc-Si film) or nanoporous silicon oxide film can be transferred to other thin films, such as SiN, $SiO_2$, $Al_2O_3$, high temperature oxides, single-crystal Si, or other materials, by using the a nanoporous silicon film (e.g., pnc-Si film) or nanoporous silicon oxide film as a mask during a reactive ion etching (RIE) process. RIE uses a chemically-reactive plasma to remove material and the chemistry of the RIE may vary depending on the thin film material. During this transfer, the open pores of the pnc-Si or silicon oxide allow incident ions to remove material from the SiN film while the nanocrystalline regions of the pnc-Si protect the SiN. Besides removing material from the SiN film, the RIE may also thin the pnc-Si or silicon oxide. The pnc-Si or silicon oxide may remain on the SiN or may be completely removed from the SiN during the RIE. For example, gases such as $CF_4$, $CHF_3$, $SF_6$, and Ar, can be used during RIE. Additionally, gases such as $O_2$ and $H_2$ can be used in combination with the aforementioned gases during RIE.

The pores in the SiN may correspond to the position of the pores in the pnc-Si. In an example, the pores are a near copy of each other.

Removing the pnc-Si layer may provide more consistency in the resulting SiN nanoporous film. For example, the residual mask may be non-uniform following the etch. Removing the residual mask may reveal a clean or uniform surface.

Lateral etch propagation may be affected by the interface between the oxide and nitride and/or Si. Thus, the type of these materials may be optimized. For example, $SiO_2$ may be formed using TEOS, thermal processes, or sputter deposition at various thicknesses. The $SiO_2$ may have a thickness between approximately 25 nm and 250 nm. The thickness of the sacrificial oxide may vary between approximately 25 nm and 150 nm.

Use of RIE allows a range of pore sizes and porosities to be formed in SiN films. The pore size and/or porosity of the resulting SiN film can be larger, smaller, or the same as that of the nanoporous silicon or silicon oxide mask.

Some factors that affect the pore transfer process and resulting pore geometry include the etch time, the chamber pressure, the source gases used, and the ratio of the various source gases used. Shorter etch times may lead to pore sizes that are comparable or less than that of the template material, such as that of the pnc-Si. Shorter etch times also may leave the pnc-Si or silicon oxide as a nanoporous cap on the SiN. In the case of pnc-Si, this cap may be used as a hydrophilic glass-like surface. Longer etch times may lead to pore side-wall erosion and, consequently, larger pore sizes and higher porosity in the SiN than the pnc-Si or silicon oxide.

Increases in chamber pressure may decrease anisotropy and may result in larger pore sizes and porosity.

Some source gases affect Si (or silicon oxide) differently from SiN. For example, $CF_4$ etches Si faster than SiN while $CHF_3$ reduces the etch rate of Si compared to SiN. This may be because the hydrogen in $CHF_3$ increases the etch resistance of Si, but does not affect the etch rate of SiN. In contrast, Ar etches materials using a physical mechanism independent of the material being etched, which results in anisotropic etching. Various ratios of the source gases may be optimized to obtain particular results. Additional gases also may be used. For example, $O_2$ may be used as an etchant to remove any fluoropolymers that form from the $CF_4$ and $CHF_3$ used for etching.

In an embodiment, $XeF_2$ gas is used to remove the residual pnc-Si mask from the SiN. $XeF_2$ has a 2000:1 etch selectivity between Si and $SiO_2$ or SiN. Thus, less SiN is etched during this process, which may increase the overall strength of the membrane.

The pnc-Si or silicon oxide mask can be removed by the etch process. In an embodiment, the pnc-Si or silicon oxide mask is completely removed during the etch process. In another embodiment, at least a portion of the pnc-Si or silicon oxide mask remains after the etch process. In the case of a pnc-Si mask, the remaining pnc-Si can form a hydrophilic cap on the nanoporous SiN layer. The cap may help the SiN surface become more hydrophilic. This cap also may provide better wetting properties for the SiN membrane or increase overall permeance. SiN may be hydrophobic, which may impede water from passing through the pores. Rendering the SiN hydrophilic through the presence of this cap may reduce or eliminate this characteristic of some SiN membranes.

The nanoporous SiN membrane also may be released from the surface of a Si wafer by supporting the SiN membrane with a polymer-based scaffold and chemically etching an adhesive $SiO_2$ that bonds the SiN membrane to the Si wafer. This process can be referred to as a "lift-off" process. This polymer scaffold may provide more flexibility to the membrane sheet than SiN scaffolds. The SiN membrane and scaffold may be configured to release together so that the SiN membrane and scaffold remain intact during processing.

In an embodiment, a photosensitive polymer such as photoresist is used to pattern a scaffold on the membrane top side. This may create, in an example, an 80% porous scaffold. An etch is performed through the pores of the membrane using a BOE to preferentially etch the $SiO_2$ at a >200:1 ratio compared to the SiN membrane. Thus, the $SiO_2$ etches significantly faster than SiN whereas pnc-Si is not etched by the BOE. In another embodiment, vapor phase HF is used to chemically etch the $SiO_2$ and release the SiN membrane.

The SiN membrane can be released using other methods. The layer under the SiN membrane may be Si or the Si wafer and an $XeF_2$ etch may be used to remove the Si in contact with the SiN. This would release the membrane in a dry etch process, which may provide a yield increase compared to some wet etch processes. In an example, a layer of polysilicon is disposed between the SiN membrane and a $SiO_2$ layer. The polysilicon layer is dissolved by the $XeF_2$ and the SiN membrane floats off the $SiO_2$ layer.

The concentration of BOE or vapor phase HF and the etch time can be optimized to remove the sacrificial oxide without compromising the SiN membrane. BOE has a high etch selectivity for $SiO_2$ compared to SiN. This selectivity may be approximately >200:1. Prolonged exposure to BOE may result in thinning and pore enlargement of Si or SiN membranes because BOE will eventually etch SiN during this prolonged exposure. Etching SiN by 10 nm or more may enlarge and merge pores to the point that membrane strength is affected, though other factors also may play a role in the membrane strength.

An inorganic scaffold instead of a polymeric scaffolds may be used in another alternate embodiment. Such inorganic scaffolds can be used in aggressive solvent systems or at temperatures greater than, for example, approximately 300° C. Use of such inorganic scaffolds may enable these membranes to be used in the environments common to, for example, solid oxide fuel cells, nanoparticle production, hydrogen production, heterogeneous catalysis, or emissions control. Examples of inorganic scaffold materials include $SiO_2$, SiN, Si, SiC, $Al_2O_3$, and other materials known to those skilled in the art. Inorganic scaffolds may be formed using methods such as, for example, soft lithography, LPCVD, or plasma-enhanced chemical vapor deposition (PECVD). Soft lithography may involve use of "green" state ceramic precursors and may create a scaffold pattern directly followed by drying and heat treatment (e.g., calcining). Certain types of chemical vapor deposition (CVD) may be followed by lithographic treatments to create the desired scaffold pattern.

In an embodiment, an oxide may be deposited or grown on the nanoporous SiN membrane to improve cell adhesion and wettability of the membrane. Etching during production of the SiN membrane may remove any capping pnc-Si, so the presence of this oxide may promote cell attachment to the SiN membrane. Alternatively, an extracellular matrix coating may be used to promote cell attachment to the SiN membrane instead of the oxide layer.

The properties and characteristics of the SiN membrane, including pore size, may vary as disclosed herein with the potential application. In an embodiment, the properties of the SiN, such as stress, thickness, or Si content, can be tuned or altered during manufacturing to suit a particular application. For example, strength of the SiN membrane may be increased by increasing the thickness. In another example, tensile strength may be increased to make the SiN membrane tighter and more resistant to deflection.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

In another aspect, the present disclosure provides uses of an SiN membrane. The nanoporous SiN membranes can be used in a variety of applications. These membranes may be used in, for example, laboratory separation devices, multi-well cell culture devices, electronic biosensors, optical biosensors, active pre-concentration filters for microfluidic devices, hemodialysis devices, or other applications.

The SiN membrane may be designed for sieving nanoparticles ranging in size from 5 nm to 100 nm or protein ladders from 5 kD to 100 kD. Higher membrane areas may result in a larger capacity to filter high protein concentrations before clogging. This may enable new uses for SiN membranes during protein separations. In another application, cell growth or viability of cells may be tested on an SiN membrane. In yet another application, the SiN membranes are used to create membrane arrays for cell culture in 24, 48, or 96 well plate formats. These formats may be used for high throughput screening. By producing large-area SiN membranes for the formats, new cell-based drug screens may be performed. For example, drug permeability across cell cocultures designed to mimic tissue barriers, such as blood-brain or air-blood barriers, may be tested. SiN membranes may improve results or enable new testing because the membranes that separate these cells in vivo may only be approximately 20 nm thick.

The SiN membrane may be designed for sensing of biological polymeric molecules such as nucleic acids and proteins, or to characterize interactions among such biological polymeric molecules and other biological or small synthetic molecules. For example, the pores within an SiN membrane may be used for electronic sensing methods for DNA genotyping and to characterize ligand-receptor binding, protein-nucleic acid, or small molecule-nucleic acid interactions. The pores within an SiN membrane also may be used for optical sensing methods to characterize ligand-receptor binding and protein-nucleic acid or small molecule-nucleic acid interactions. In another example, the SiN membrane may be designed as an active pre-concentrating filter of molecules in a microfluidic device. In such an example, the pores within an SiN membrane could be used as a nanofluidic transistor to control analyte capture and the SiN membrane may serve as a gating electrode, having been coated with a conducting metal.

The membranes can be used in filtration applications, such as hemodialysis. In an embodiment, a method of removing waste products (e.g., creatinine, urea, and free water) from blood comprises contacting blood having one or more waste products above a desired concentration with a membrane of the present invention such that the concentration of the one or more waste products is lowered to a desired level. The blood may be from an individual (e.g., a human or non-human animal). In this application, it is expected that the thinness and high transport efficiency of the SiN membrane will enable hemodialysis to be implemented with a much smaller filtration element, allowing for smaller systems for home dialysis or even wearable/portable units. It is also possible that the length of time required to complete a dialysis session would be reduced due to the high rate of transport of the waste products from the blood into the dialysate stream. Other characteristics of the SiN, such as its increased strength and low binding to proteins in the blood make it desirable for applications involving blood. In an embodiment, a hemodialysis device comprises a SiN membrane. Examples, of suitable hemodialysis devices are known in the art.

Of course, other variations to the embodiments disclosed herein are possible. The exact porosity and pore diameter may vary. Larger pores may be beneficial for some applications, though high porosity or merger of pores may be avoided for certain applications because it may cause weakening of the SiN membrane.

The following examples are presented to illustrate the present disclosure. They are not intended to be limiting in any manner.

Example 1

Figure 1:
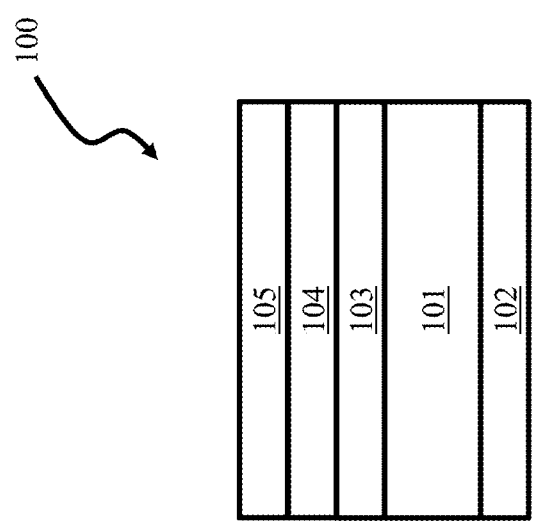

FIGS. 1-5 are schematic representations of a first example of an SiN membrane manufacturing process. In FIG. 1, the substrate 100 included Si layer 101, SiN layer 102, SiN layer 103, amorphous silicon (a-Si) layer 104, and $SiO_2$ layer 105. In this example, the SiN layer 102 and SiN layer 103 were both approximately 50 nm in thickness, the a-Si layer 104 was approximately 40 nm in thickness, and the $SiO_2$ layer 105 was approximately 20 nm in thickness, though other dimensions are possible. The capping $SiO_2$ layer keeps the a-Si layer from agglomerating/deforming during the thermal annealing step that forms the pnc-Si. In FIG. 2, a thermal process, such as a rapid thermal processing (RTP) step, has been performed. The a-Si layer 104 of FIG. 1 was converted to a pnc-Si layer 200 using this thermal process. The pnc-Si layer 200 contains pores 201 (illustrated in black). These pores 201 may be approximately 5 nm to 80 nm in dimension. While only four pores 201 are illustrated, this is merely for ease of illustration. Thus, besides converting the crystal structure, the RTP forms the pores 201 in the pnc-Si layer 200. After the thermal process, the pnc-Si layer 200 was approximately 40 nm in thickness in this example, though other dimensions are possible.

Figure 3:
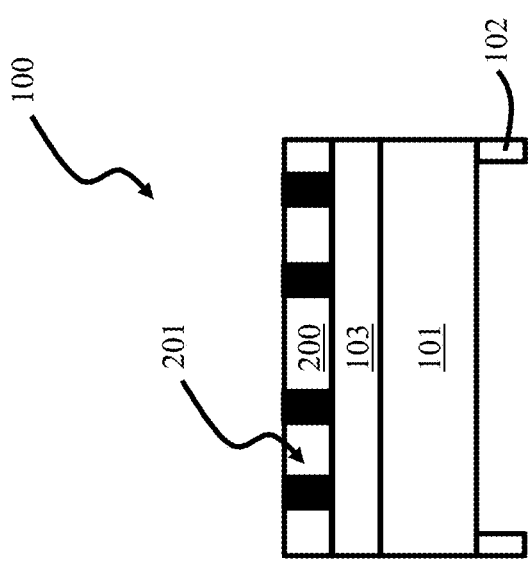

In FIG. 3, the SiN layer 102 was patterned to expose part of the Si layer 101 and the $SiO_2$ layer 105 was removed using 10:1 BOE solution.

Figure 4:
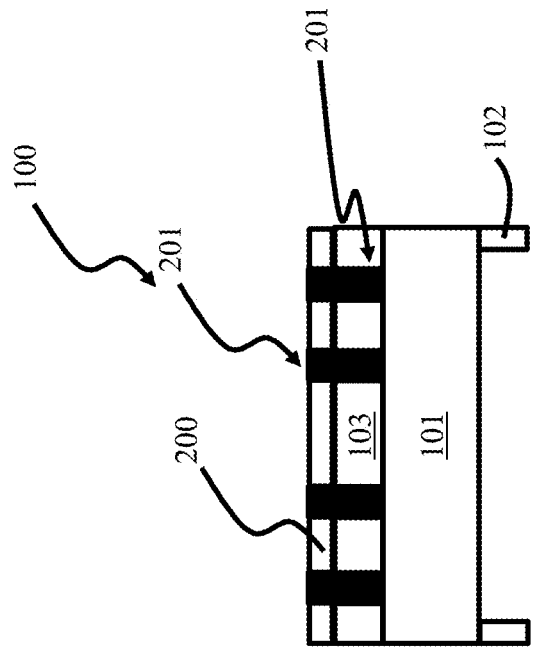

In FIG. 4, the RIE was performed. Pores 201 were etched in the SiN layer 102 through the pores 201 in the pnc-Si layer 200. The RIE removed some or all of the pnc-Si layer 200. In this example, some of the pnc-Si layer 200 remained on the SiN layer 102 after completion of the RIE. Alternatively, all of the pnc-Si layer 200 may be completely removed.

Figure 5:
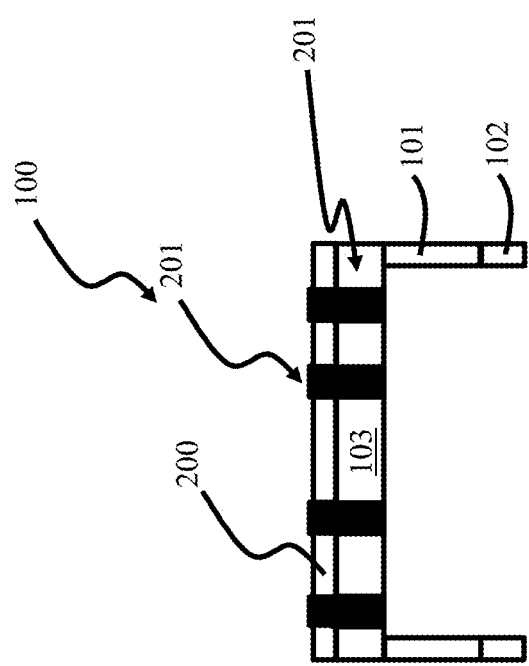

In FIG. 5, an additional etch step was performed. This may be, for example, a KOH or EDP etch that removes a portion of the exposed Si layer 101. The actual shape of the remaining Si layer 101 may be curved or angled rather than perpendicular to the SiN layer 102 as illustrated. An optional tetraethyl orthosilicate (TEOS) layer may be formed on the SiN layer 102 on the remaining pnc-Si layer 200 opposite of the Si layer 101. The substrate 100 as illustrated in FIG. 5 may then be used for various applications.

Example 2

Figure 7:
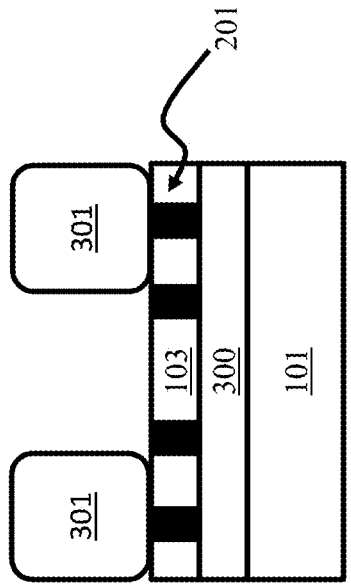
FIGS. 6-8 are schematic representations of a second example of an SiN membrane manufacturing process.
Figure 6:
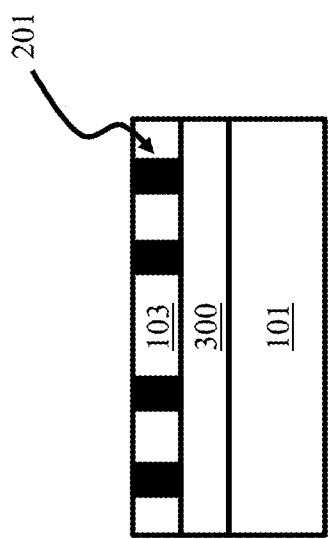
Figure 8:
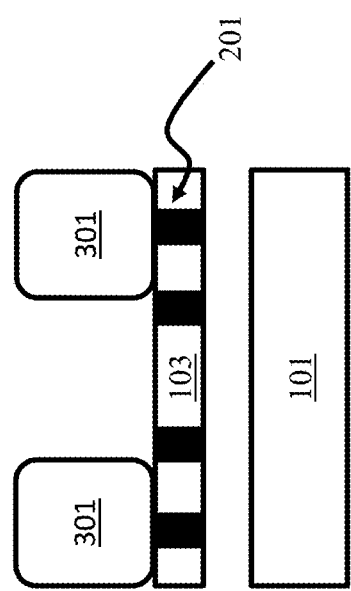

FIGS. 6-8 are schematic representations of a second example of an SiN membrane manufacturing process. The example of FIGS. 6-8 may be combined with steps from Example 1 or may be a standalone process. This example may be referred to as a "lift-off" process. In FIG. 6, the pores 201 (illustrated in black) in the SiN layer 103 were formed using an RIE. The pnc-Si layer was completely removed from the surface of the SiN layer 103 during this RIE. A sacrificial $SiO_2$ layer 300 was formed between the Si layer 101 and the SiN layer 103 prior to formation of the SiN layer 103.

A scaffold 301 was applied to the SiN layer 103 in FIG. 7. The scaffold 301 was SU-8 photoresist (3010 series manufactured by Microchem International), though other materials are possible. This scaffold 301 was formed by spin coating the SU-8 photoresist to a thickness of 10 μm on top of the membrane, patterning the SU-8 photoresist to form an 80% open scaffold using contact photolithography, and developing the SU-8 photoresist to have a desired pattern.

In FIG. 8, a BOE etch was performed to remove the sacrificial $SiO_2$ layer 300. The SiN layer 103 was no longer connected to the Si layer 101 after the BOE etch. Instead, the SiN layer 103 was connected only to the scaffold 301. This scaffold 301 may be used to manipulate, transport, or hold the SiN layer 103. In an example, an area of approximately 1 $mm^2$ was lifted off the Si wafer and floated atop the etchant solution without any noticeable delamination and with all the membranes remaining intact.

Figure 10:
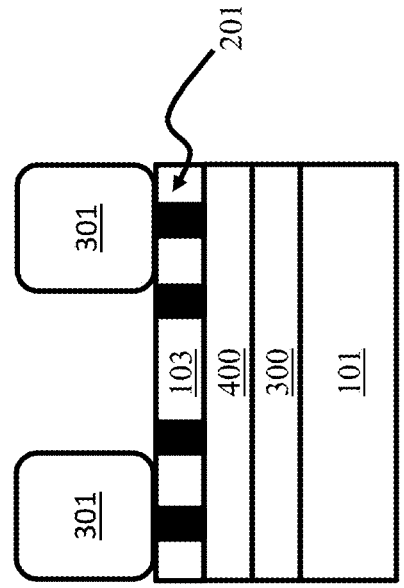
FIGS. 9-11 are schematic representations of a third example of an SiN membrane manufacturing process.
Figure 9:
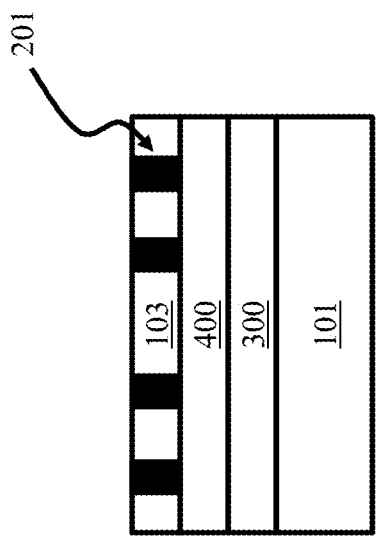
Figure 11:
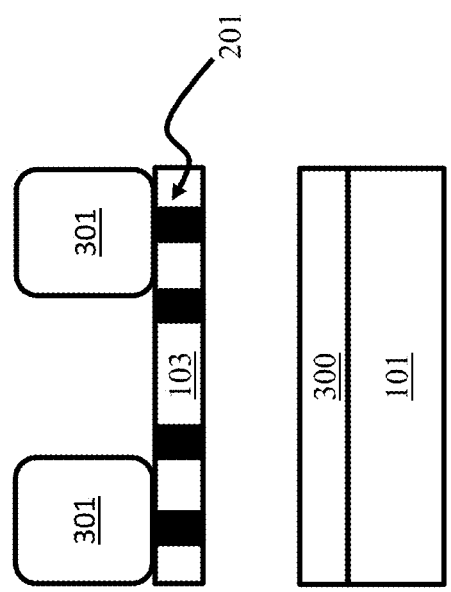

FIGS. 9-11 are schematic representations of a third example of an SiN membrane manufacturing process. The example of FIGS. 9-11 may be combined with steps from Example 1 or may be a standalone process. This example may be referred to as a "lift-off" process. In FIG. 9, the pores 201 (illustrated in black) in the SiN layer 103 were formed using an RIE. The pnc-Si layer was completely removed from the surface of the SiN layer 103 during this RIE. A sacrificial silicon layer 400 was formed between the $SiO_2$ layer 300 and the SiN layer 103 prior to formation of the SiN layer 103.

A scaffold 301 was applied to the SiN layer 103 in FIG. 10. The scaffold 301 was SU-8 photoresist (3010 series manufactured by Microchem International), though other materials are possible. This scaffold 301 was formed by spin coating the SU-8 photoresist to a thickness of 10 µm on top of the membrane, patterning the SU-8 photoresist to form an 80% open scaffold using contact photolithography, and developing the SU-8 photoresist to have a desired pattern.

In FIG. 11, a vapor phase $XeF_2$ process was performed to remove the sacrificial silicon layer 400 (shown in FIGS. 9 and 10). The SiN layer 103 was no longer connected to the $SiO_2$ layer 300 after the $XeF_2$ etch. Instead, the SiN layer 103 was connected only to the scaffold 301. This scaffold 301 may be used to manipulate, transport, or hold the SiN layer 103. In an example, an area of approximately 6 $cm^2$ was lifted off the Si wafer without any noticeable delamination and with all the membranes remaining intact.

Example 3

Figure 13:
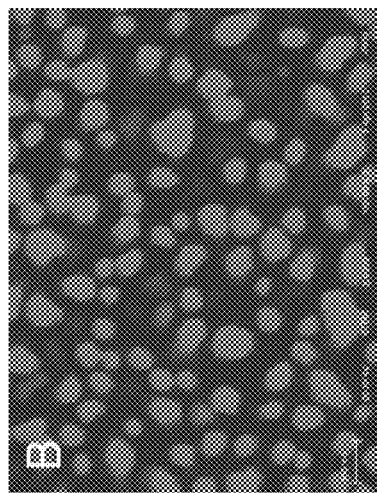
FIGS. 12-13 are STEM images of an SiN membrane and a pnc-Si mask.
Figure 12:
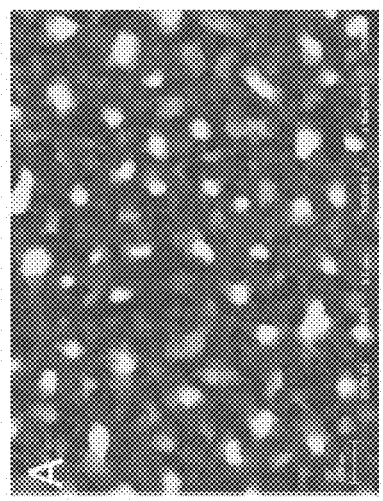

FIGS. 12-13 are STEM images of an SiN membrane and a pnc-Si mask. FIG. 12 illustrates a 40 nm thick pnc-Si film. The lighter areas in FIG. 12 are pores. FIG. 13 shows these pores transferred to a 50 nm thick SiN film using RIE of the pnc-Si mask of FIG. 12. The 40 nm pnc-Si film had an average pore diameter of approximately 38 nm and a porosity of approximately 6%. The SiN had an average pore diameter of approximately 61 nm and a porosity of approximately 30%.

Example 4

In this example, RIE was performed on SiN using a mixture of 25 sccm $CF_4$, 50 sccm $CHF_3$, 10 sccm $O_2$, and 0 sccm Ar at 100 mTorr. This resulted in an average pore size between approximately 41 nm and 46 nm and a porosity between approximately 35% and 40% in the SiN film. The high porosity may have weakened the nanoporous SiN and may have been a consequence of the isotropic behavior of the RIE recipe. Isotropic aspects of the RIE can be adjusted by changing the pressure, which in turn can increase or decrease resulting pore size and porosity in the SiN. Due to the presence of F and C in the RIE gas mixture, a thick fluoropolymer was deposited on the pnc-Si mask during the RIE transfer process, making it resistive to RIE. The presence or thickness of the fluoropolymer can be adjusted by changing the $O_2$ flow.

A second RIE was performed on SiN using a mixture of 25 sccm $CF_4$, 50 sccm $CHF_3$, 10 sccm $O_2$, and 100 sccm Ar at 50 mTorr. Ar was added to the RIE recipe to increase the anisotropic behavior of the etch. 10 sccm $O_2$ in this particular gas mixture was determined to have affected or reduced the fluoropolymer forming on the pnc-Si pore sidewalls during RIE transfer, which resulted in a more isotropic etch. One possible mechanism is that the $O_2$ scavenges the excess carbon, which may prevent formation of the fluoropolymer. Another possible mechanism is that the $O_2$ dissolves the fluoropolymer forming on the pnc-Si. Of course, other mechanisms are possible and these two mechanisms are merely listed as potential examples.

A third RIE was performed on SiN using a mixture of 25 sccm $CF_4$, 50 sccm $CHF_3$, 5 sccm $O_2$, and 100 sccm Ar at 50 mTorr. Reducing the $O_2$ flow from 10 sccm to 5 sccm allowed a thin fluoropolymer film to remain on the pnc-Si pore sidewalls. This maintained the integrity of the pore size and shape in the pnc-Si and resulted in a more anisotropic etch.

Example 5

In this example, 0 sccm $CF_4$, 50 sccm $CHF_3$, 5 sccm $O_2$, and 100 sccm Ar were used for RIE on SiN. Due to the presence of F and C in the gas mixture, a thin fluoropolymer deposited on the pnc-Si pore sidewalls, but this fluoropolymer did not deposit thick enough to keep the Si from dissolving. By eliminated the $CF_4$ gas, better selectivity between the SiN and pnc-Si was achieved because the etch rate of Si was slowed and the etch became more anisotropic. Such a recipe could be used to manufacture thicker nanoporous membranes such as, for example, a SiN membrane that is approximately 50 nm in thickness.

Example 6

Figure 14:
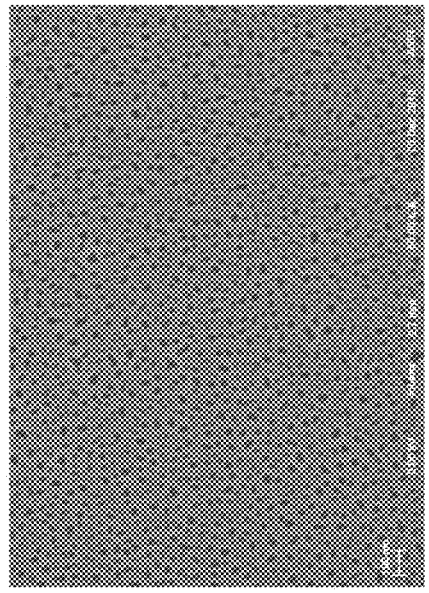
FIG. 14 includes a table of images showing variations in pore size at differing chamber pressures.
Figure 14:
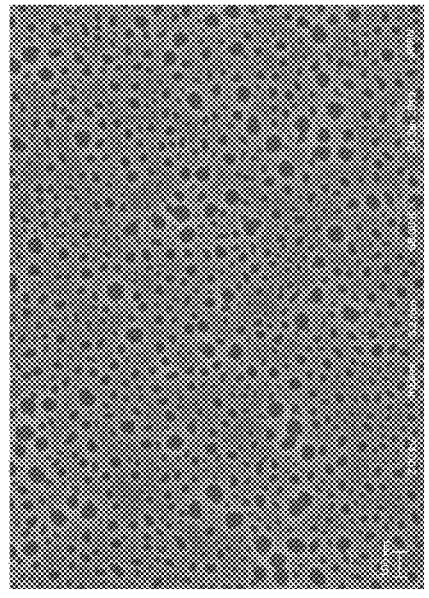
Figure 14:
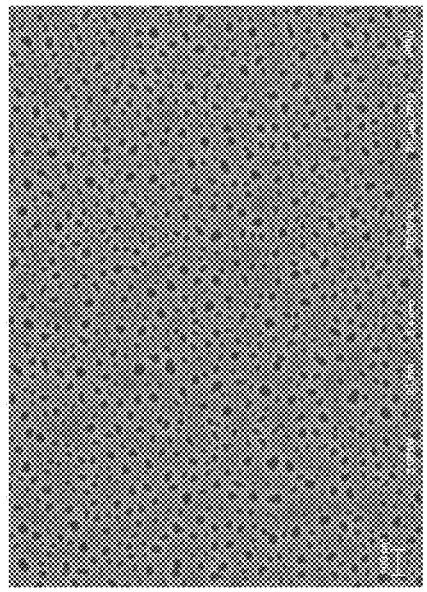
Figure 14:
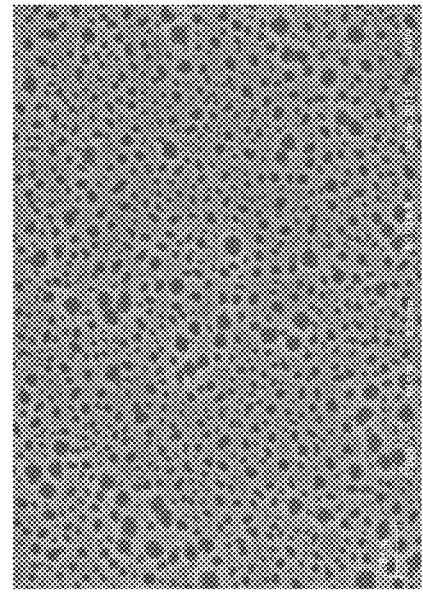

In this example, pressure was varied during RIE of a 50 nm SiN membrane. FIG. 14 includes a table of images showing variations in pore size at differing chamber pressures. The SiN wafer perimeter and center are illustrated in FIG. 13. As seen in the images, increased pressure resulted in decreased anisotropy and increased pore size. There was reasonable uniformity across the wafer, which indicates that this process may be scalable to larger substrates.

Example 7

Figure 15:
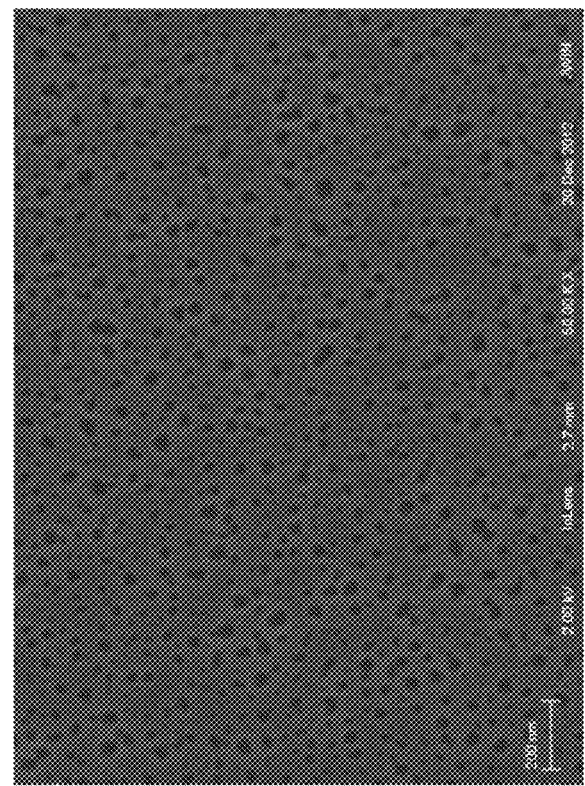
FIG. 15 includes a second table of images showing variations in pores size at differing chamber pressures.
Figure 15:
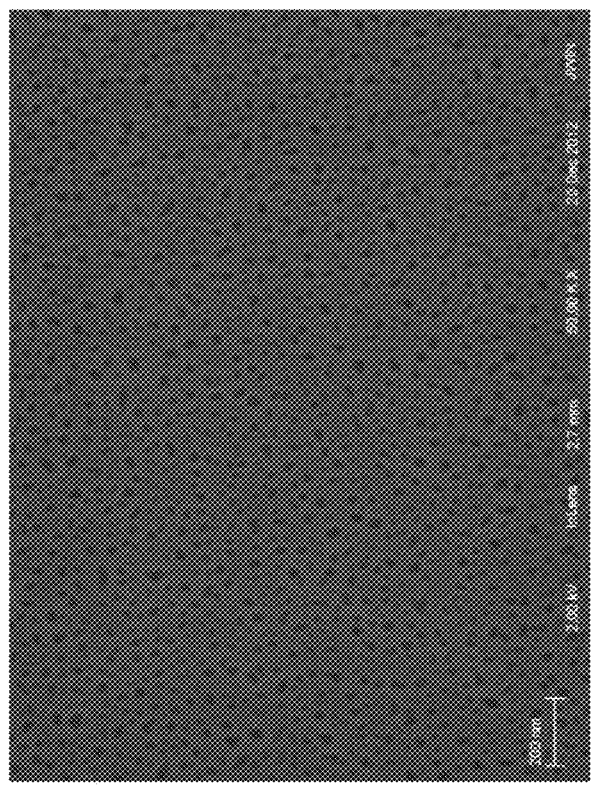

In this example, pressure was varied during RIE of a 20 nm SiN membrane. FIG. 15 includes a second table of images showing variations in pores size at differing chamber pressures. As seen in the images, the SiN membrane has increased pore size at increased pressure.

Example 8

In this example, cell growth on SiN membranes was tested. Slides were pre-incubated with growth media for five minutes and bEnd3 (P23) were plated onto the slides. The slides were stained with Calcein AM (green-live) and EtBr (red-dead) and imaged under the microscope. The cells showed similar morphology when grown on pnc-Si.

Example 9

Figure 16:
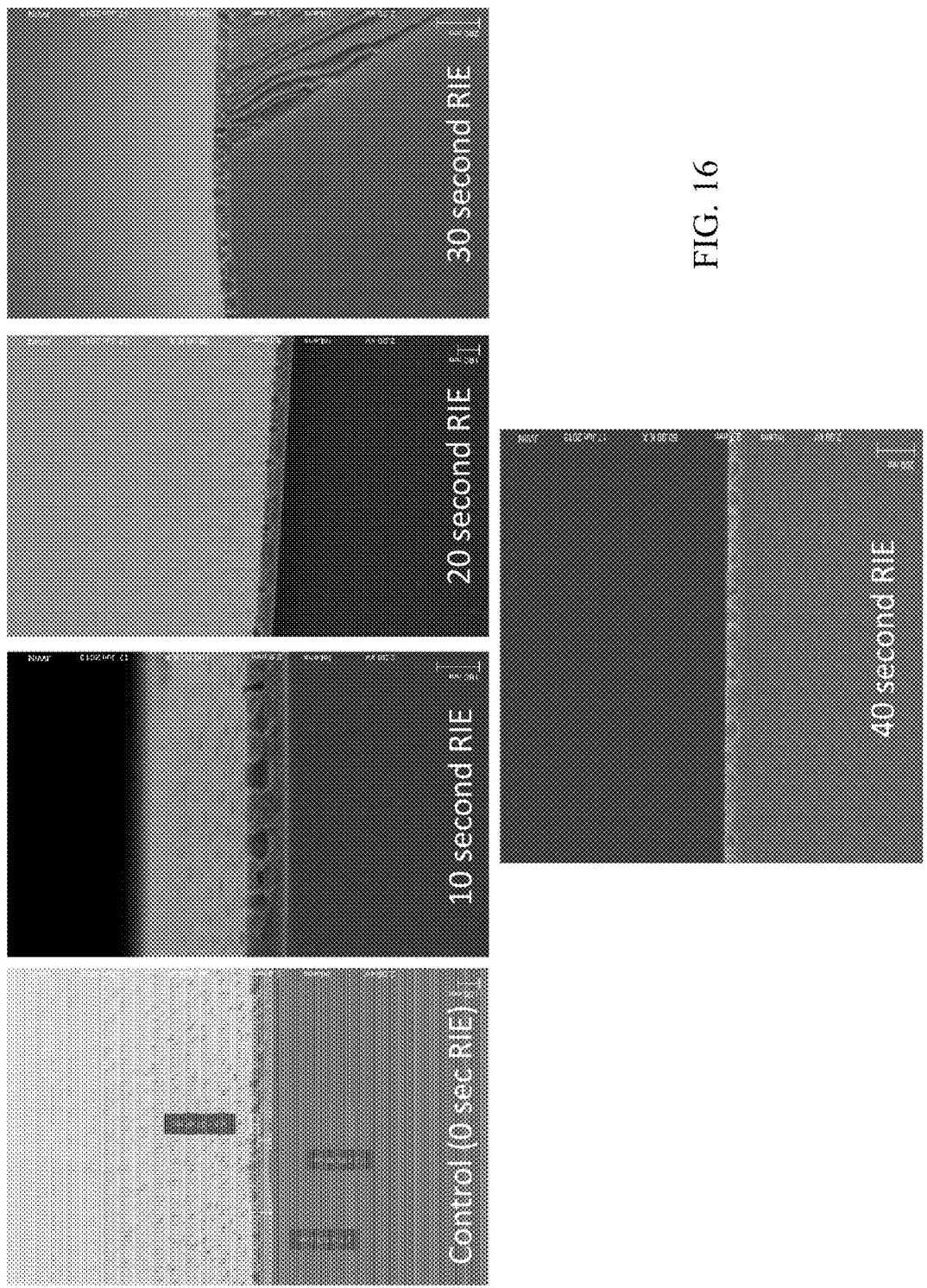
FIG. 16 includes a third table of images showing SEM cross-sections of a 40 nm pnc-Si film on a 50 nm SiN film in different stages of a process.

In this example, SEM cross-sections were taken of 40 nm pnc-Si on 50 nm SiN, as illustrated in FIG. 16. The first image shows the film stack prior to the RIE transfer etch. Subsequent images show a time evolution of the RIE transfer process in 10-second increments as the etch transfers the nanopores from the pnc-Si mask to the SiN while dissolving away the pnc-Si. Note the conical geometry in some of these cross-sectional images. This property can be controlled by optimizing the RIE etch parameters of chamber pressure, gas mixtures, and process time.

Although the present invention has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:

1. A method for forming a nanoporous SiN layer comprising the steps of:
   forming a porous nanocrystalline silicon (pnc-Si) layer or porous silicon oxide layer that is disposed on an SiN layer; and
   etching said SiN layer by reactive ion etching such that a nanoporous SiN layer is formed; and
   wherein the porous silicon oxide layer is formed from a porous nanocrystalline silicon (pnc-Si) layer.

2. The method of claim 1, wherein the reactive ion etching uses an etch gas mixture comprising $CHF_3$, $O_2$, and Ar.

3. The method of claim 2, wherein the etch gas mixture further comprises $CF_4$.

4. The method of claim 1, wherein the reactive ion etching uses an etch gas mixture comprising 50 sccm $CHF_3$, 5 sccm $O_2$, and 100 sccm Ar.

5. The method of claim 1, wherein the reactive ion etching uses an etch gas mixture comprising $CHF_3$, $O_2$, and Ar at a $CHF_3$:$O_2$:Ar ratio of 10:1:20.

6. The method of claim 1, wherein said reactive ion etching uses an etch gas mixture comprising 25 sccm $CF_4$, 50 sccm $CHF_3$, and 10 sccm $O_2$; or 25 sccm $CF_4$, 50 sccm $CHF_3$, 10 sccm $O_2$, and 100 sccm Ar; or 25 sccm $CF_4$, 50 sccm $CHF_3$, 5 sccm $O_2$, and 100 sccm Ar.

7. The method of claim 1, wherein said reactive ion etching uses an etch gas mixture comprising $CF_4$, $CHF_3$, $O_2$, and Ar at a $CF_4$:$CHF_3$:$O_2$:Ar ratio of 5:10:2:0; 5:10:2:20; or 5:10:1:20.

8. The method of claim 1, wherein said reactive ion etching is performed at a chamber pressure of 50, 100, or 300 mTorr.

9. A method for forming a monolithic nanoporous SiN layer comprising the steps of:
   forming pores in an SiN layer using a pnc-Si layer or a porous silicon oxide layer formed from a pnc-Si layer, wherein said SiN layer is disposed on a first layer; and
   removing said first layer such that a monolithic nanoporous SiN layer is formed; and
   wherein the porous silicon oxide layer is formed from a porous nanocrystalline silicon (pnc-Si) layer.

10. The method of claim 9, wherein the said first layer comprises a silicon wafer, which serves as a substrate.

11. The method of claim 9, wherein removing said first layer comprises using one of KOH, tetramethyl-ammonium hydroxide, or ethylene diamine pyrocatechol.

12. The method of claim 9, wherein said forming of a nanoporous SiN layer comprises using a method comprising the steps of:
   forming a porous nanocrystalline silicon (pnc-Si) layer or porous silicon oxide layer that is disposed on an SiN layer; and,
   etching said SiN layer by reactive ion etching such that a nanoporous SiN layer is formed.

13. A method for forming a free-standing nanoporous SiN layer comprising the steps of:
   forming pores in an SiN layer, wherein said SiN layer is disposed on a first layer and said first layer is disposed on a second layer, and said second layer is disposed on a third layer;
   forming a scaffold layer on an SiN layer following formation of pores within said SiN layer; and
   removing said first layer from between said SiN layer and said second layer such that a free-standing nanoporous SiN layer is formed; and
   wherein said forming of a nanoporous SiN layer comprises using a method comprising the steps of:
      forming a porous nanocrystalline silicon (pnc-Si) layer or porous silicon oxide layer that is disposed on an SiN layer; and
      etching said SiN layer by reactive ion etching such that a nanoporous SiN layer is formed; and
      wherein the porous silicon oxide layer is formed from a porous nanocrystalline silicon (pnc-Si) layer.

14. The method of claim 13, wherein the said first layer comprises poly-crystalline silicon, which serves as a sacrificial layer, the said second layer comprises silicon dioxide, which serves as an etch stop, and the said third layer comprises a silicon wafer, which serves as a substrate.

15. The method of claim 13, wherein said scaffold is selected from the group consisting of a photoresist, a polymer, a metal, $SiO_2$, SiN, Si, SiC, and $Al_2O_3$.

16. The method of claim 13, wherein removing said first layer comprises using $XeF_2$.

17. The method of claim 13, wherein said third layer further comprises a material selected from the group consisting of stainless steel, $Al_2O_3$, $SiO_2$, glass, fused silica, Al, polytetrafluoroethylene, and polyethylene terephthalate.

* * * * *